United States Patent

Hersh et al.

[11] Patent Number: 5,590,662
[45] Date of Patent: Jan. 7, 1997

[54] DETECTION OF OSCILLOMETRIC BLOOD PRESSURE COMPLEXES USING CORRELATION

[75] Inventors: Lawrence T. Hersh; John W. Booth, both of Tampa, Fla.

[73] Assignee: Johnson & Johnson Medical, Inc., New Brunswick, N.J.

[21] Appl. No.: 389,711

[22] Filed: Feb. 15, 1995

[51] Int. Cl.$^6$ .................................................. A61B 5/02
[52] U.S. Cl. ............................................................ 128/681
[58] Field of Search .................................. 128/681, 680, 128/682, 687, 683, 677; 364/413.03

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/681 |
| 4,627,440 | 12/1986 | Ramsey III et al. | 128/682 |
| 4,638,810 | 1/1987 | Ramsey III et al. | 128/681 |
| 4,754,761 | 7/1988 | Ramsey III et al. | 128/683 |
| 4,774,960 | 10/1988 | Arnold et al. | 128/681 |
| 4,777,959 | 10/1988 | Wallach et al. | 128/677 |
| 4,889,133 | 12/1989 | Nelson et al. | 128/681 |
| 4,926,873 | 5/1990 | Frankenreitter | 128/681 |
| 4,949,710 | 8/1990 | Dorsett et al. | 128/680 |
| 4,984,577 | 1/1991 | Frankenreiter | 128/681 |
| 5,052,397 | 10/1991 | Ramsey III et al. | 128/682 |
| 5,054,495 | 10/1991 | Uemura et al. | 128/680 |
| 5,103,833 | 4/1992 | Apple | 128/687 |
| 5,170,795 | 12/1992 | Ramsey III et al. | 128/682 |
| 5,218,968 | 6/1993 | Apple | 128/687 |
| 5,253,648 | 10/1993 | Walloch | 128/681 |
| 5,261,413 | 11/1993 | Kawahara | 128/682 |
| 5,280,790 | 1/1994 | Brooks | 128/681 |
| 5,311,872 | 5/1994 | Apple | 128/687 |
| 5,390,679 | 2/1995 | Martin | 128/713 |

*Primary Examiner*—Angela D. Sykes
*Assistant Examiner*—Eric F. Winakur
*Attorney, Agent, or Firm*—Woodcock Washburn Kurtz Mackiewicz & Norris

[57] ABSTRACT

An automated sphygmomanometer which stores the attributes for all oscillation complexes at each pressure step and compares the stored waveform data to a template containing the attributes of a "clean" oscillation complex from a present or previous NIBP determination or from a standard template determined from a broad population of patients. Preferably, an oscillation complex near MAP is selected as the template. After the oscillation complexes have been gathered, correlation values for each new oscillation complex in the stored waveform data and the template are calculated using correlation calculations from detection theory. All oscillation complexes which highly correlate with the template (their correlation values are above a given threshold) are maintained as "good" oscillation data, while the remainder of the oscillation complexes are ignored as corrupted by artifact data. Artifact-reduced data may then be used in the blood pressure calculation. Similar correlation techniques are also used at each pressure step in a real-time manner to detect the presence of an oscillation complex during a step inflate or deflate blood pressure measurement.

28 Claims, 11 Drawing Sheets

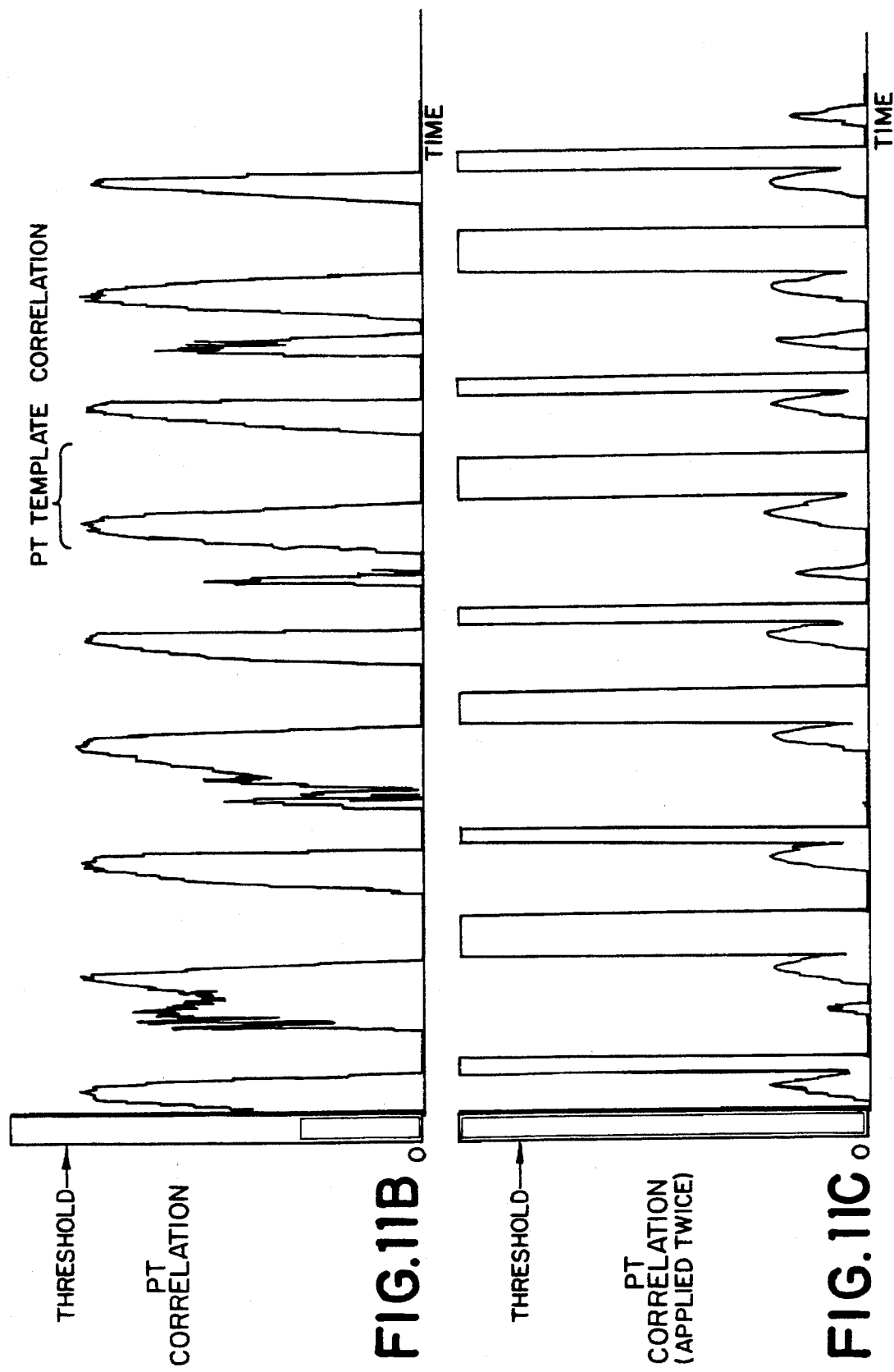

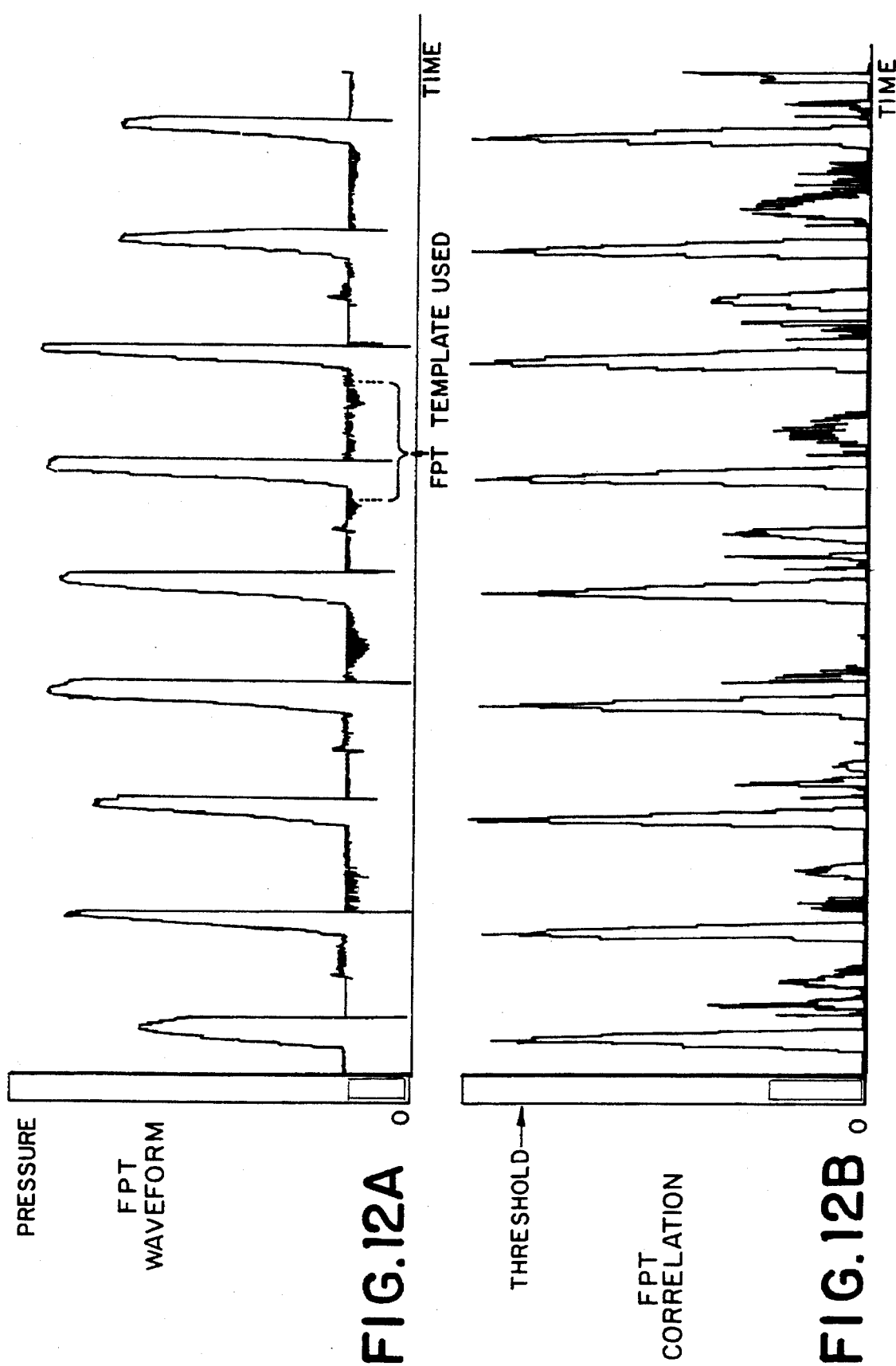

ns. In addition,
a source of pressurized air 109 is connected via a duct 110
through an inflate valve 111 and a duct 112 to the pressure
cuff 101. The inflate valve 111 is electrically controlled
through a connection 113 from the microprocessor 107.
Also, the deflate valve 102 is connected by duct 114 via a
branch connection 115 with the duct 112 leading to cuff 101.

During operation of the apparatus illustrated in FIG. 1, air
under pressure to about 8–10 p.s.i. is typically available in
the source of pressurized air 109. When it is desired to
initiate a determination of blood pressure, the microprocessor 107 furnishes a signal over path 113 to open the inflate
valve 111. The deflate valve 102 is closed. Air from the
source 109 is communicated through inflate valve 111 and
duct 112 to inflate the cuff 101 to a desired level, preferably
above the estimated systolic pressure of the patient. Microprocessor 107 responds to a signal on path 106 from the
pressure transducer 104, which is indicative of the instantaneous pressure in the cuff 101, to interrupt the inflation of
the cuff 101 when the pressure in the cuff 101 reaches a
predetermined value above the estimated systolic pressure of
the patient. Such interruption is accomplished by sending a
signal over path 113 instructing inflate valve 111 to close.
Once inflate valve 111 has been closed, the blood pressure
measurement can be obtained by commencing a deflate
routine.

Microprocessor 107 processes the signals from pressure
transducer 104 to produce blood pressure data and to reject
artifact data as described in the afore-mentioned Ramsey
'029 and '034 patents. The blood pressure may be determined in accordance with the teachings of Medero et al. in
U.S. Pat. No. 4,543,962, of Medero in U.S. Pat. No. 4,546,
775, of Hood, Jr. et al. in U.S. Pat. No. 4,461,266, of
Ramsey, III et al. in U.S. Pat. No. 4,638,810, of Ramsey, III
et al. in U.S. Pat. No. 4,754,761, of Ramsey, III et al. in U.S.
Pat. No. 5,170,795, and of Ramsey, III et al. in U.S. Pat. No.
5,052,397, all of which are commonly assigned herewith
and the disclosures of which are hereby incorporated by
reference. Any of these known techniques are used to
determine the quality of the oscillation complexes received
at each level so that the blood pressure determination is
made using actual blood pressure data and not artifact data.

Actual measurement of the blood pressure under the
control of the microprocessor 107 and the deflate valve 102
and as sensed by pressure transducer 104 can be accomplished in any suitable manner such as that disclosed in the
aforementioned patents or as described below. At the
completion of each measurement cycle, the deflate valve
102 can be re-opened long enough to relax the cuff pressure
via exhaust 103. Thereafter, the deflate valve 102 is closed
for the start of a new measurement cycle.

Accordingly, when a blood pressure measurement is
desired, the inflate valve 111 is opened while the cuff
pressure is supervised by pressure transducer 104 until the
cuff pressure reaches the desired level. The inflate valve 111
is then closed. Thereafter, the deflate valve 102 is operated
using signal 108 from microprocessor 107 and the blood
pressure measurement taken.

Prior art FIG. 2 illustrates a pressure versus time graph
illustrating a conventional cuff step deflation and measurement cycle for a conventional NIBP monitor. As illustrated,
the cuff 101 is inflated to a pressure above the systolic
pressure, and the cuff 101 is then step deflated to the next

DETECTION OF OSCILLOMETRIC BLOOD PRESSURE COMPLEXES USING CORRELATION

FIELD OF THE INVENTION

This invention relates to automated blood pressure monitoring, and more particularly, to automated blood pressure monitors that utilize a pneumatic cuff for accomplishing a sphygmomanometric measurement on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith and incorporated by reference, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, pressure fluctuations are monitored. The resultant arterial pulse signals typically consist of a DC voltage with a small superimposed variational component caused by arterial blood pressure pulsations (referred to herein as "oscillation complexes" or just simply "oscillations"). The oscillation complexes typically have amplitudes which are about one percent that of the arterial pulse signals. After suitable filtering to reject the DC component and to provide amplification by a scale factor, peak amplitudes of the oscillations above a given base-line are measured and stored. As the decrementing continues, the peak amplitudes will normally increase from a lower level to a relative maximum, and thereafter will decrease. These amplitudes form an oscillometric envelope for the patient. The lowest cuff pressure at which the oscillations have a maximum value has been found to be representative of the mean arterial pressure ("MAP") of the patient. Systolic and diastolic pressures can be derived either as predetermined fractions of the oscillation size at MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator usually sets a time interval, typically from 1 to 90 minutes, at which blood pressure measurements are to be made. The noninvasive blood pressure ("NIBP") monitor automatically starts a blood pressure determination at the end of the set time interval.

FIG. 1 illustrates a simplified version of the oscillometric blood pressure monitor described in the aforementioned Ramsey patents. In FIG. 1, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. The deflation of cuff 101 via deflate valve 102 is controlled by microprocessor 107 via control line 108.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing.

pressure level. A timeout duration d is provided at each step during which the signal processing circuitry searches for oscillation complexes in accordance with the techniques described in the afore-mentioned commonly assigned patents or as described below. At the end of timeout duration d, the cuff pressure is decremented even if no oscillation complex is detected. This process of decrementing the pressure and searching for oscillation complexes is repeated at least until MAP and/or the oscillometric envelope 200 may be calculated. The entire blood pressure determination process is then repeated at intervals set by the user, some other predetermined interval, or manually.

As shown in FIG. 2, the patient's arterial blood pressure forms an oscillometric envelope 200 comprised of a set of oscillation amplitudes measured at the different cuff pressures. From oscillometric envelope 200, systolic, MAP and diastolic blood pressures are typically calculated. However, as noted in the afore-mentioned patents, it is desired that all artifact data be rejected from the measured data so that oscillometric envelope 200 contains only the desired amplitude data and no artifacts, thereby improving the accuracy of the blood pressure determinations.

Generally, conventional NIBP monitors of the type described in the afore-mentioned patents use oscillation amplitude matching at each pressure level as one of the ways to discriminate good oscillations from artifacts. In particular, pairs of oscillations are compared at each pressure level to determine if they are similar in amplitude and similar in other attributes, such as shape, area under the oscillation curve, slope, and the like. If the oscillations compare within predetermined limits, the average amplitude and cuff pressure are stored and the pressure cuff is deflated to the next pressure level for another oscillation measurement. However, if the oscillations do not compare favorably, the attributes of the earlier oscillation are typically ignored and the attributes of the latter oscillation are stored. The monitor does not deflate; instead, the monitor waits for another oscillation to compare with the one that was stored. This process continues until two successive oscillations match or a time limit is exceeded.

Unfortunately, by ignoring the earlier oscillation in favor of the later oscillation for comparison to a subsequent oscillation, it is possible that a "good" oscillation will be ignored in favor of an oscillation containing an artifact. The oscillation with the artifact then will not compare favorably with subsequent oscillations, and the monitor will deflate to the next level without finding a "good" oscillation.

It is thus desired to save all oscillations at each pressure level and to compare new oscillations with a "good" oscillation so that it can be quickly determined if the new oscillation contains artifacts.

It is further desired to use a "good" oscillation as a template for comparison to other oscillations using correlation techniques so that shape data can be used in the analysis of the received waveform.

It is also desired to further eliminate artifacts at the end of each blood pressure measurement by eliminating artifact data using correlation techniques.

SUMMARY OF THE INVENTION

The present invention relates to an automated sphygmomanometer with improved techniques for artifact reduction using correlation i.e., by comparing how well two signals agree in pattern as time progresses. In accordance with the invention, the attributes for all oscillation complexes at each pressure step are stored and compared to a template, which is a standard to which the waveform in question must be similar in order for there to be a high correlation. In accordance with the invention, the template contains the attributes of a "clean" oscillation complex from a previous NIBP determination taken at a "quiet" time or from any step of the present NIBP data acquisition process. Preferably, an oscillation complex near MAP for a relatively quiet determination is selected as the template. On the other hand, a standard template determined from a broad population of patients may be used as the template, where the standard template may be adjusted as a function of heart rate. Correlation values for each new oscillation complex and the template are calculated using correlation calculations from detection theory. All oscillation complexes which highly correlate with the template (their correlation values are above a given threshold) are recognized as "good" oscillation data, while the remainder of the oscillation complexes are ignored as corrupted by artifact data.

In a first embodiment of the invention, the correlation analysis is performed on the data acquired during a "normal" step deflate NIBP data acquisition process in which all the oscillation complex data at each level is stored and the monitor decrements when two oscillation complexes (not necessarily consecutive) match using known matching criteria. In other words, all cuff pressure waveform samples acquired during the NIBP data acquisition process are stored. A template is identified as a "clean" complex from the present or a previous NIBP data acquisition process or as a standard template, and correlation values for a moving time window along the cuff waveform are calculated using the identified template. A threshold for the correlation values is determined based on the amount of noise and the degree of correlation, and oscillation complexes are identified as starting at those maximum points where the waveforms have correlation values which exceed the correlation threshold. As desired, the threshold may be adjusted until the detected heart beat periods fall to within some range or until a suitable blood pressure envelope is found.

In a second embodiment of the invention, a template is correlated with the cuff waveform as the samples are collected at each pressure level. The correlation values are computed as the blood pressure data acquisition process progresses and are used to determine if enough data has been collected at a given cuff pressure level so that the monitor may deflate to the next level. For example, if an oscillation complex has a correlation value above a predetermined threshold, then that oscillation complex is stored and the monitor deflates the cuff to the next pressure level. Preferably, the template is adapted from oscillation to oscillation as the blood pressure data acquisition process progresses. In other words, once a new oscillation complex has been identified, it can be used as the new template for further signal processing during the data acquisition/step deflate process. Of course, further artifact rejection may be obtained by combining this embodiment with the first embodiment to provide post-measurement processing as well.

The technique of the invention expands upon previous techniques by using the shape or pattern of all or portions of the oscillation complex rather than just the amplitude peak or area of the oscillation complex in the determination of the presence of an oscillation complex. Also, processing attributes of oscillation complexes at the end of the last pressure level before the blood pressure is calculated allows a list of good samples to be acquired for the blood pressure calculation, permitting better discrimination of oscillations from artifacts because more is known about what the oscillation attributes should be for a given pressure level in the context of the oscillation attributes at all pressure levels. As a result, a blood pressure determination may continue at high levels of artifact and still give good blood pressure results so long as enough good samples are found during post-processing.

BRIEF DESCRIPTION OF THE DRAWINGS

The present invention will be better understood after reading the following detailed description of the presently preferred embodiments thereof with reference to the appended drawings, in which:

FIG. 8 illustrates a flow chart for minimizing artifacts in the blood pressure data using correlation in accordance with the second embodiment of the invention.

FIGS. 12 (A) and (B) illustrate a correlation determination for a template determined from an oscillation complex (FPT) waveform removed from the PT waveform from the pressure transducer.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 3–12. Those skilled in the art will readily appreciate that the description given herein with respect to those figures is for explanatory purposes only and is not intended in any way to limit the scope of the invention. Also, common reference numbers are used throughout the drawings to represent common elements. All questions regarding the scope of the invention should be resolved by referring to the appended claims.

As noted above with respect to FIGS. 1 and 2, the oscillometric technique for determining blood pressure operates by measuring arterial pulse amplitudes at respective sample cuff pressures. The resulting pulse amplitude samples form an oscillometric envelope 200 from which MAP and the diastolic and systolic pressures may be calculated. In accordance with the invention, however, MAP and the diastolic and systolic pressures are calculated from blood pressure samples which have been screened for artifacts using correlation techniques. Such techniques in accordance with the invention will be described below with respect to FIGS. 3–12.

Figure 1:
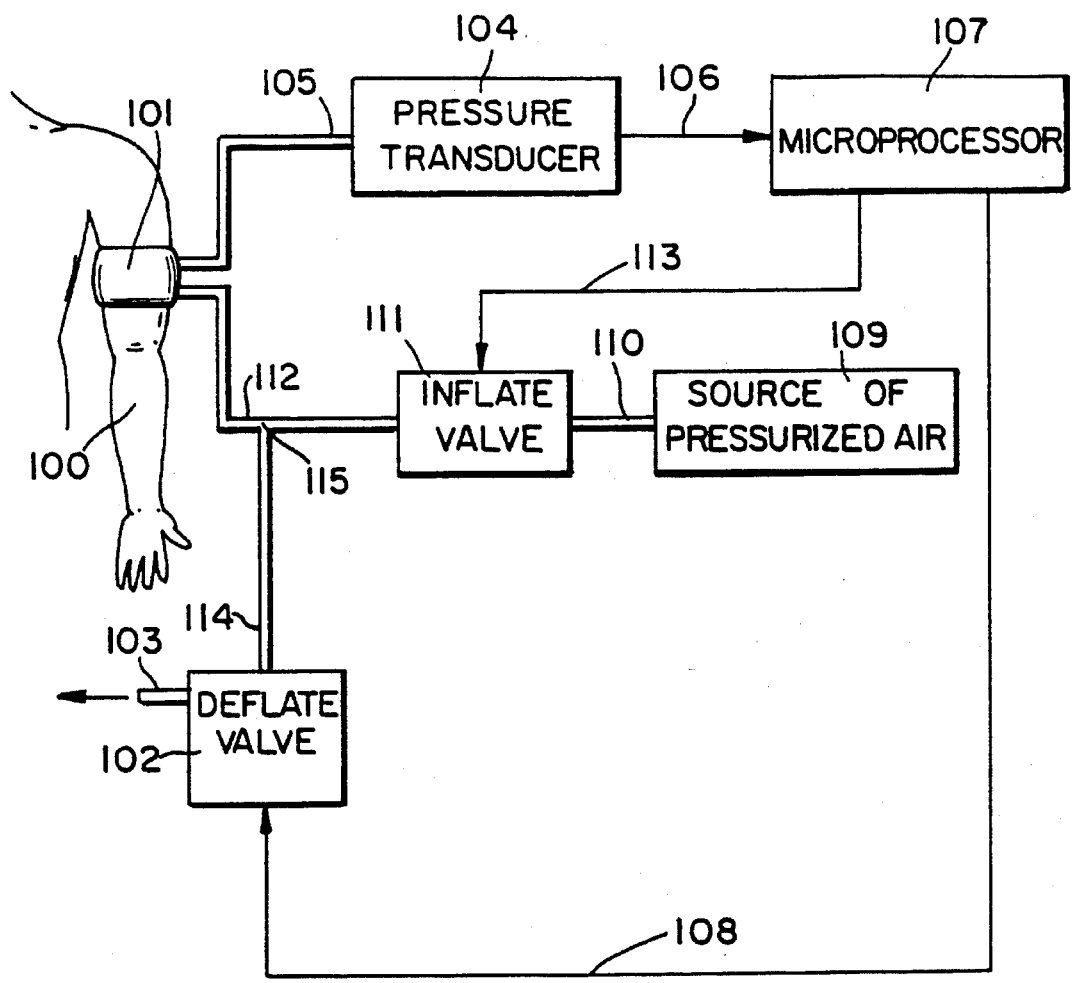
FIG. 1 is a schematic representation of a conventional noninvasive blood pressure ("NIBP") monitor of the type to which the present invention is directed.
Figure 2:
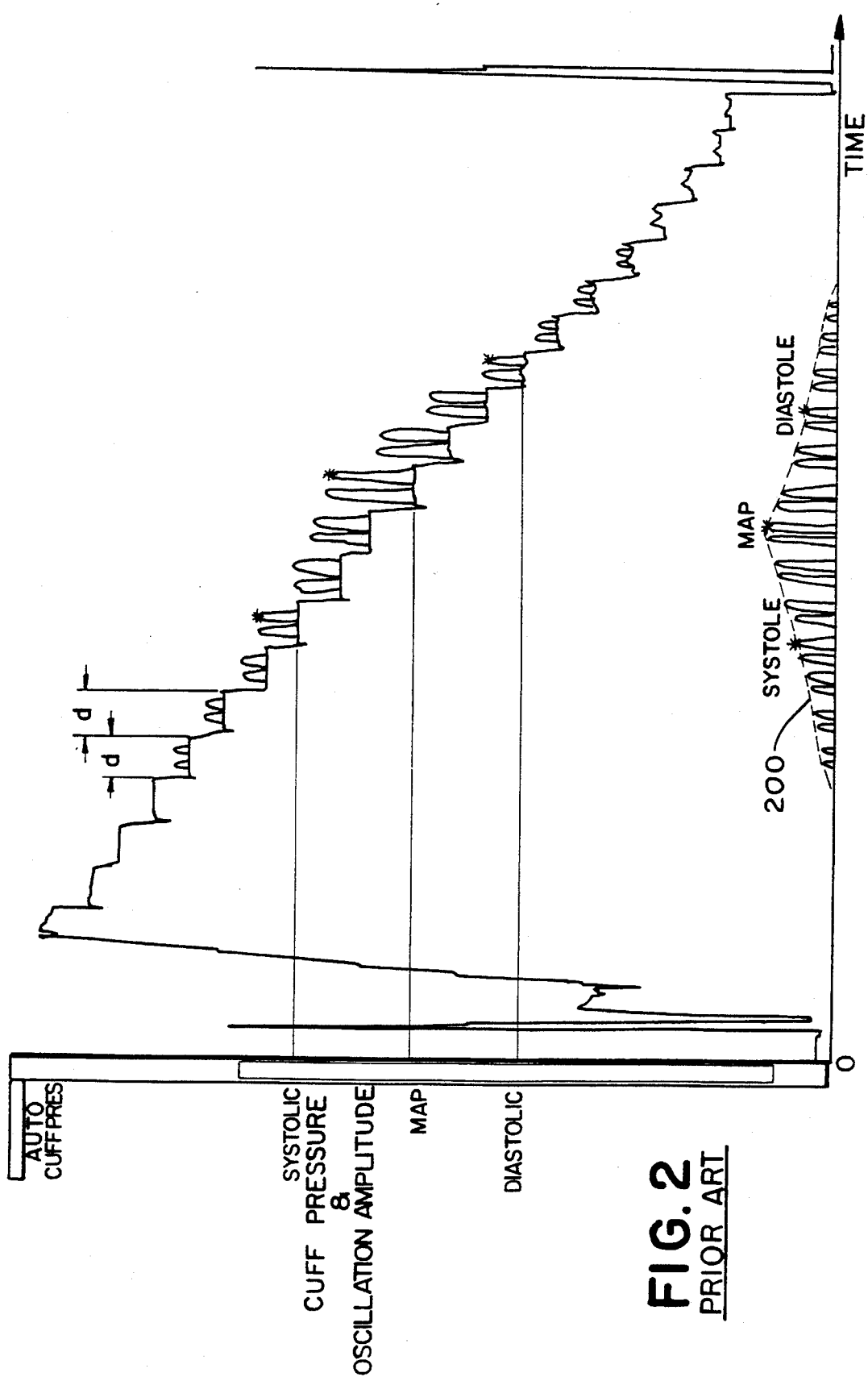
FIG. 2 is a pressure versus time graph illustrating a measuring cycle including step deflation steps and the corresponding oscillation complexes measured using the conventional NIBP monitor of FIG. 1.
Figure 3:
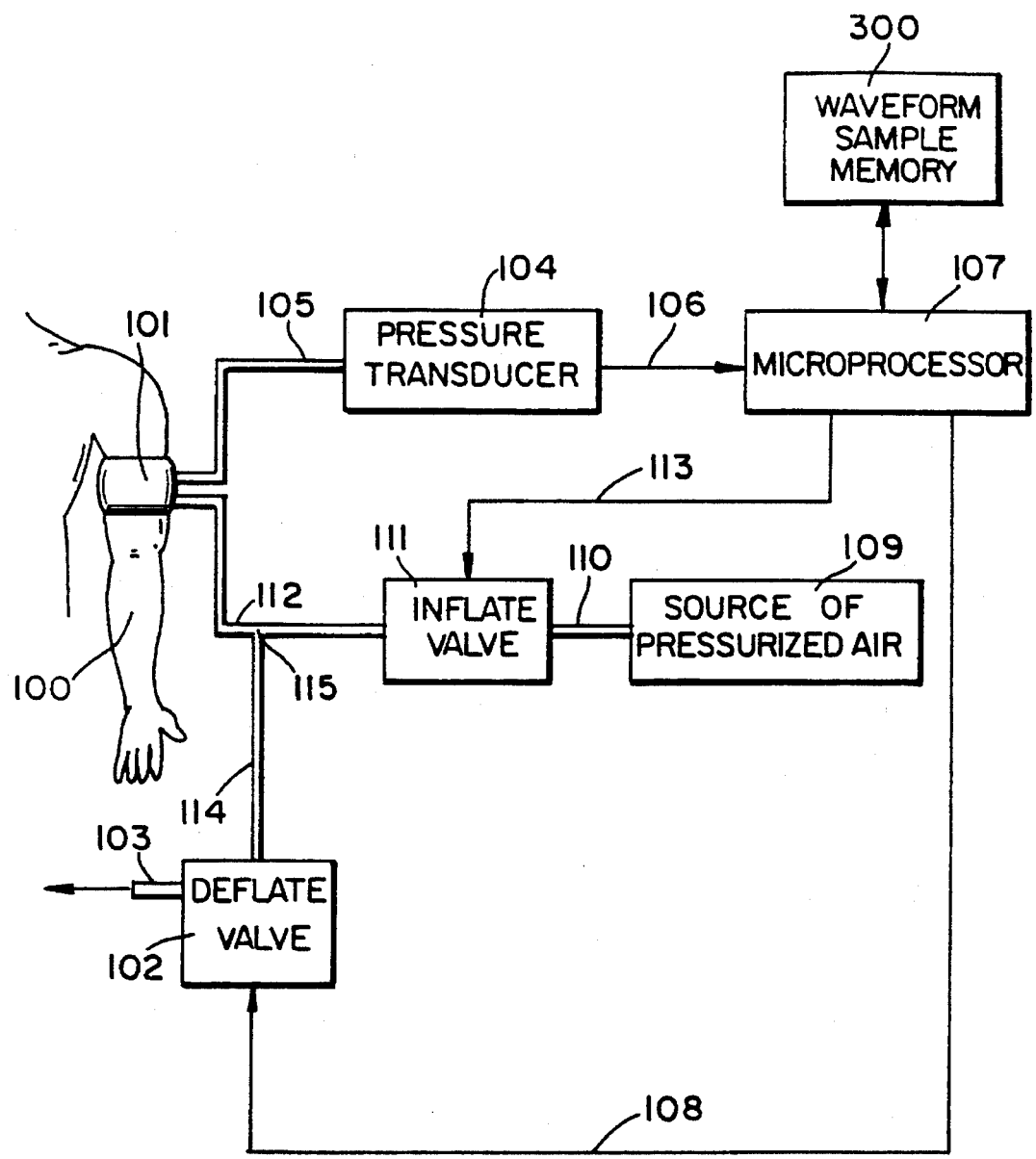
FIG. 3 is a schematic representation of a noninvasive blood pressure ("NIBP") monitor having a waveform memory which stores an input waveform for correlation processing in accordance with the invention.

FIG. 3 illustrates the oscillometric blood pressure monitor of FIG. 1 modified to include a waveform sample memory 300 which saves the attributes for all oscillation complexes at each pressure step to allow comparison of previous oscillation complexes with new oscillation complexes using the correlation techniques of the invention. By storing the attributes (samples) for all oscillation complexes, the monitor can match oscillations to the shape and characteristics of known oscillations which occurred previously at the same pressure level, previously during the same NIBP determination, or during one or more previous NIBP determinations. Correlation techniques allow such known oscillations to be used as a template setting forth the shape characteristics for known oscillations, thereby allowing oscillations to be recognized even in the presence of numerous artifacts. As a result, correlation may be used to allow earlier detection of oscillation complexes and hence earlier deflation during an NIBP step deflation measurement or for greater artifact rejection during post-measurement processing.

As noted above, the present invention provides improved identification of blood pressure complexes during an oscillometric blood pressure data acquisition process using correlation calculations. The present inventors have found that optimal oscillation complex detection may be accomplished for patients with arrhythmias and artifacts by applying detection theory principles used in correlation techniques. Such principles are well known to those skilled in the art and are well described in Chapter 4 of the text entitled "Detection, Estimation, and Modulation Theory," Harry L. Van Trees, John Wiley, 1968, pp. 239–422.

In accordance with a first embodiment applying correlation in accordance with the invention, the entire blood pressure waveform acquired during the data acquisition/step deflate cycle is analyzed in a conventional manner and the resulting envelope 200 is stored. Then, at the end of the data acquisition/step deflate cycle but before the actual blood pressure calculation, the stored envelope 200 is further processed using correlation to remove all artifact data from the envelope 200. In other words, the stored data is compared against a known oscillation complex such as the oscillation complex found at MAP in the current or a previous NIBP determination using a "sliding time window" approach as in detection theory. If a high degree of correlation is found between the signals at a particular instant in time, it is determined that an oscillation complex starts with the current waveform sample. Of course, such a technique requires all cuff pressure waveform samples measured by pressure transducer 104 during the blood pressure data acquisition process to be stored in waveform sample (buffer) memory 300. Accordingly, waveform sample memory 300 is designed to hold at least twice the largest number of samples that might occur during the step deflation measurements, thus allowing memory for determining the template and for performing the waveform processing in accordance with the invention.

As just noted, the stored waveform data is compared to a known oscillation waveform, which functions as a template for the shape of the waveform. Typically, the template is identified by first performing a standard step deflate NIBP data acquisition process for detecting the presence of an oscillation complex. The time length of the template is generally proportional to the heart period. Preferably, the oscillation from around MAP for a chosen NIBP determination is used as the template since it is generally least affected by artifacts. The identified template is then used to compute the correlation value for every sample along the pressure cuff waveform and the points with the highest degree of correlation are identified. The maximum of those points with a correlation value above some predetermined threshold is determined to represent the beginning of an oscillation complex, unless it is determined that respective maximums are too close together for the latter maximum to be the beginning of another oscillation complex.

In a presently preferred embodiment, the calculation of a correlation value for each waveform sample and the comparison of the resulting correlation value to a threshold requires the correlation value to be normalized, typically to a value between −1 and +1. Hence, a threshold at, e.g., 0.8 and above indicates a high degree of correlation. On the other hand, those skilled in the art will appreciate that correlation may be determined without normalizing the correlation values. In this case, correlation techniques of the type used in standard detection algorithms may be used whereby the measured energy of the received signals are absorbed into the threshold. In other words, the template is multiplied by the waveform samples and the result is summed over the waveform. While the resulting formula is simplified, the threshold becomes function of the energy values of the waveform, template signals, and the noise and is no longer a normalized number between −1 and +1.

Figure 10:
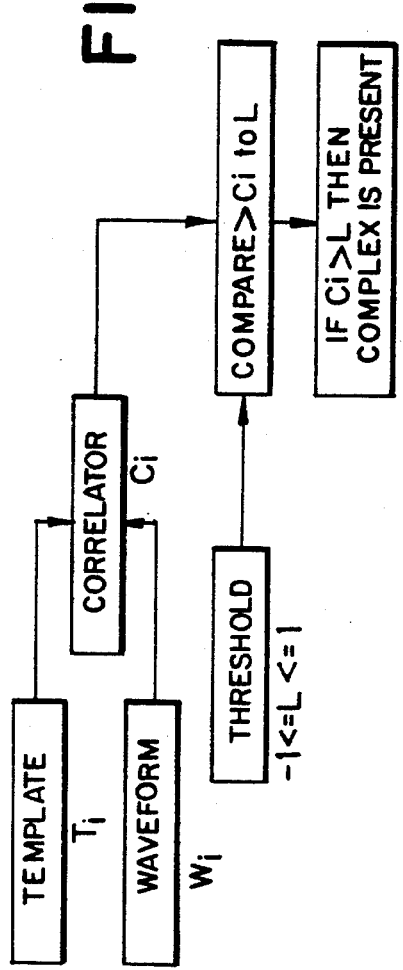
FIG. 10 illustrates the correlation calculations in accordance with the invention.

FIG. 10 illustrates the correlation calculation in accordance with the invention. As shown, the selected template waveform $T_i$ is correlated with the input waveform W to form a correlation value $C_j$ in accordance with the equation:

$$C_j = \frac{\sum_i (W_{i+j} - W_j) \cdot (T_i - T)}{\sqrt{\sum_i (W_{i+j} - W_j)^2 \cdot \sum_i (T_i - T)^2}}$$

$$\text{where } W_j = \frac{\sum_i W_{i+j}}{n} \quad T = \frac{\sum_i T_i}{n}$$

where i and j are time indices, n is the number of samples in the template, and the summations are from 1 to n. The calculated correlation value $C_j$ is then compared to a threshold L ($-1 <= L <= +1$), and it is determined that an oscillation complex is present when $C_j > L$.

On the other hand, as just noted, the correlation value can be reduced to a simpler formula:

$$C_j = \sum W_{i+j} \cdot T_i$$

where the summation over i is from 1 to n, L is a function of the energy of T, W and the noise, and the correlation value is no longer normalized to be a number between −1 and +1.

Further description of the setting of the threshold in the correlation context can be found in the afore-mentioned Van Trees text.

In a presently preferred embodiment, the normalized correlation values are calculated. Accordingly, some threshold value such as, e.g., 0.8 and above is chosen for the correlation values. The chosen threshold may be adjusted until the detected heart beat periods fall to within some range. Also, the threshold may be lowered as necessary to assure that a qualified blood pressure envelope is found in the waveform data. Oscillation complexes are then identified by determining the maximum of the correlation for each crossing of the threshold. Data below the threshold is determined not to mark the beginning of an oscillation complex. As an additional criterion, a refractory period based on the patient's pulse rate may be taken into account. During the refractory period, data for a predetermined amount of time after an oscillation complex has been identified may be ignored since it is a known biological principle that a heart beat cannot reoccur within a certain period of time. The refractory period thus can be used to reject incorrect detections due to artifacts which occur too soon after a previous oscillation detection.

Figure 4:
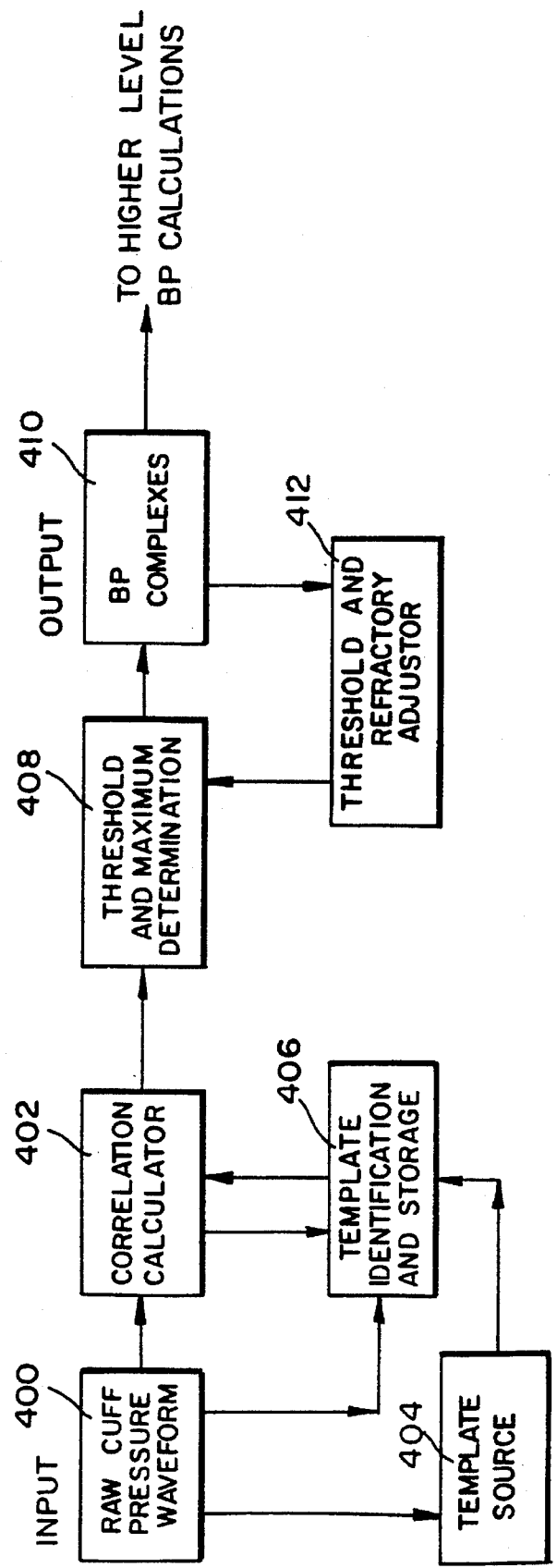
FIG. 4 illustrates the flow of data for analysis of acquired oscillation complexes using correlation techniques after the NIBP envelope data is acquired but before the actual blood pressure is calculated in accordance with a first embodiment of the invention.

FIG. 4 illustrates in summary form the data flow for the above-described post-measurement correlation technique. Generally, the illustrated data flow is provided by software implemented by microprocessor 107, although a dedicated hardware circuit may also be used to implement the illustrated algorithm.

In FIG. 4, the raw cuff pressure waveform 400 received from waveform sample memory 300 is provided to a correlation calculator 402. Correlation calculator 402 may, for example, implement Equation 1 or 2 above for $C_i$. A template which is either taken from a template source 404 such as a previous NIBP determination at a "quiet" time for the patient or detected during a previous step of the current NIBP data acquisition process is identified and stored at 406. The stored template is then provided to correlation calculator 402 for the calculation of $C_i$ for all $C_i$. The maximum of the correlation values $C_i$ for each crossing of the threshold is then determined at 408. Those samples with the maximum correlation value $C_i$ for each crossing of the threshold are determined to correspond to the beginning of an oscillation complex and are output as such at 410. Also, as desired, the threshold may be adjusted at 412 or threshold crossings are ignored during the refractory period to make certain that the detected heart beat periods fall to within a desired range.

Figure 5:
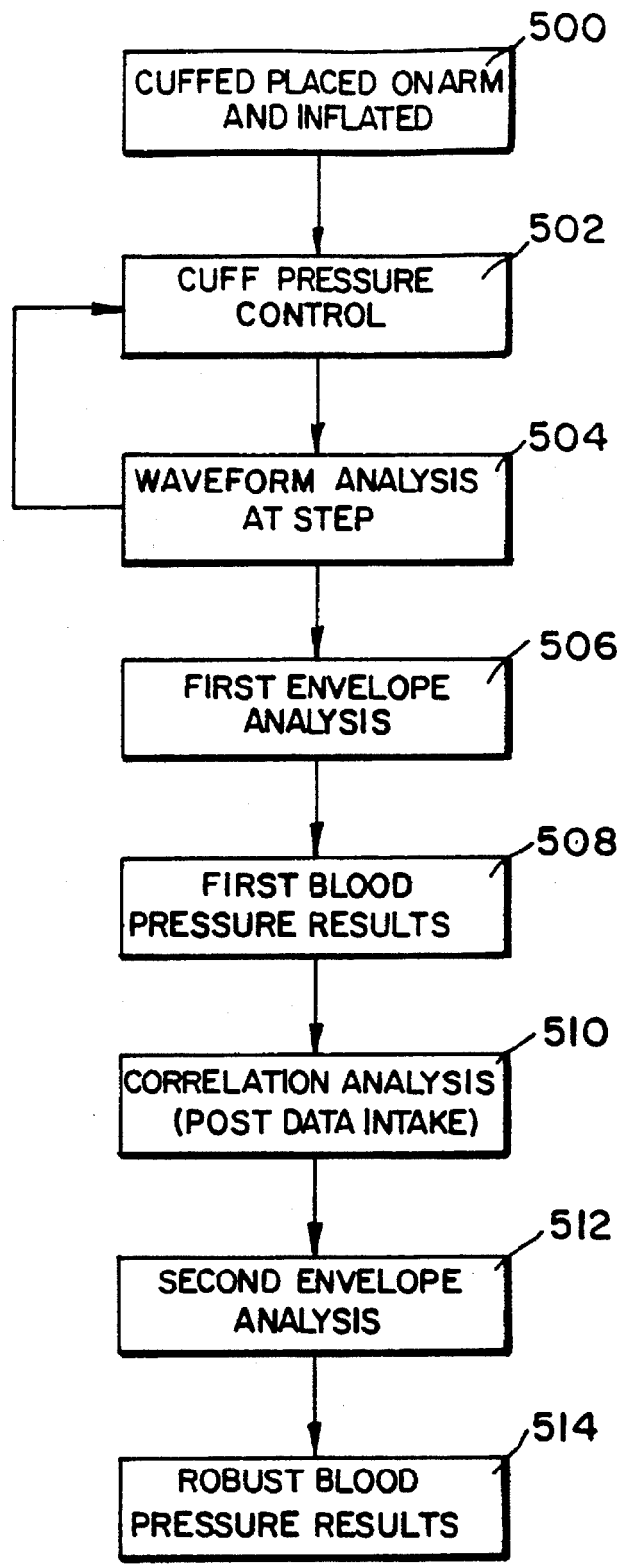
FIG. 5 illustrates a flow chart for minimizing artifacts in the blood pressure data through correlation in accordance with the first embodiment of the invention.

FIG. 5 illustrates a flow chart for minimizing artifacts in the blood pressure data in accordance with the first embodiment of the invention. As illustrated, the technique of the first embodiment requires the completion of a conventional NIBP measurement at steps 500–508 and storage of the waveform data. Then, the above-described correlation analysis is performed on all of the stored waveform data at step 510 so that additional artifacts may be eliminated. A further envelope analysis for the revised envelope (without the artifact data) is then performed at step 512 and the blood pressure calculated from the correlated data is output at step 514.

Figure 6:
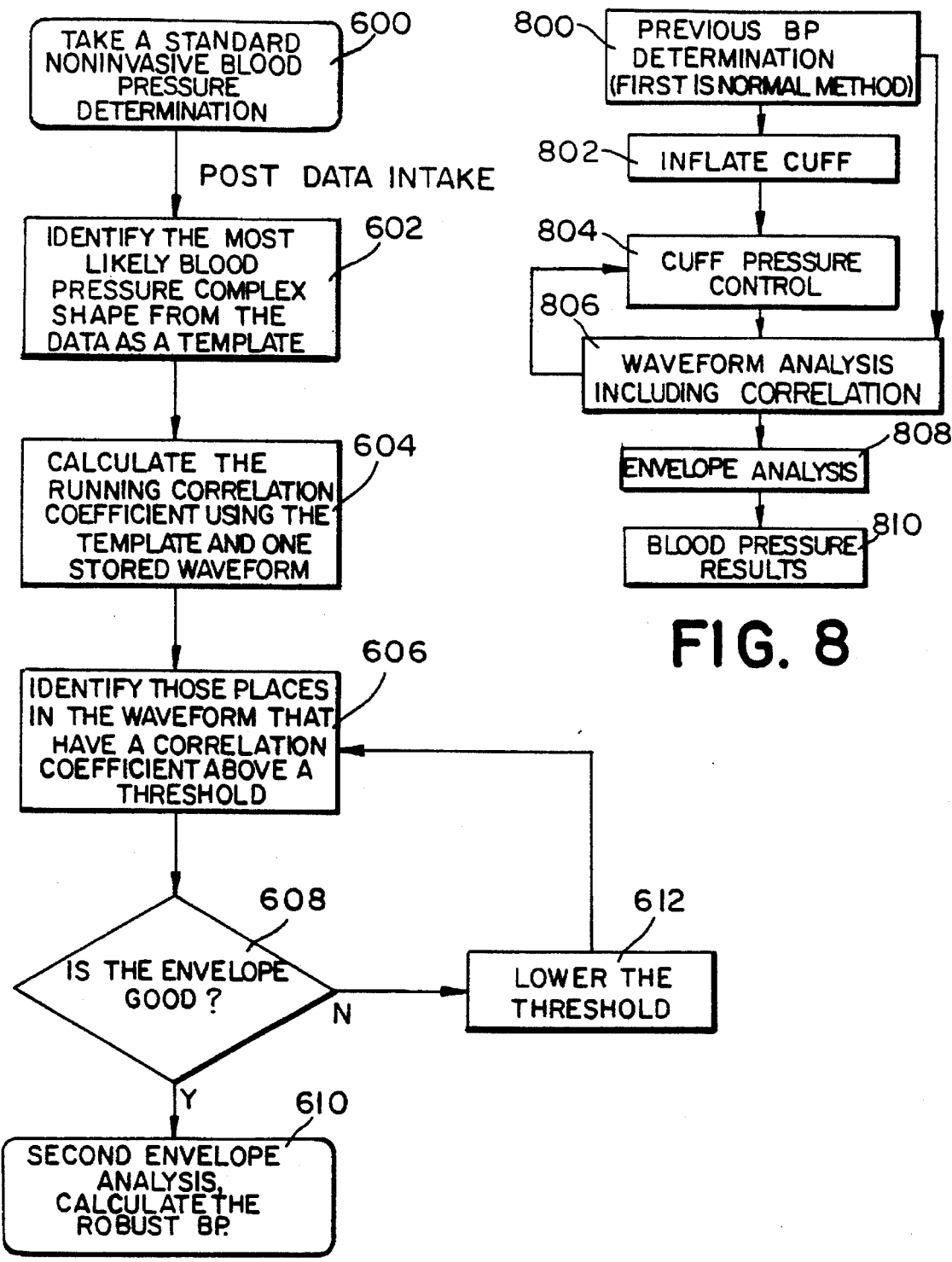
FIG. 6 illustrates a flow chart of a technique for identifying an oscillation complex in noisy conditions using correlation techniques in accordance with the first embodiment of the invention.

FIG. 6 illustrates the correlation technique of the invention with threshold adjustment. The flow chart of FIG. 6 is used to better identify an oscillation complex in noisy conditions. As shown in FIG. 6, a conventional NIBP determination is made at step 600. As shown in FIG. 5, this step includes inflating the pressure cuff above systolic pressure, step deflating and searching for oscillation complexes at each pressure level, and calculating the patient's blood pressure from the resulting envelope of oscillation complexes. In accordance with the invention, the pressure and filtered pressure waveforms as well as the calculated blood pressure values are stored in waveform sample memory 300 for post-measurement correlation processing. In other words, the correlation processing is performed after all oscillometric data is gathered.

For the correlation processing to proceed, a template is identified at step 602. The most likely complex shape typically comes from the mean arterial pressure range. Accordingly, the stored waveform data at MAP calculated and stored at step 600 may be used for the template. Of course, a more generic (standard) template determined from a combination of data from many patients may also be used. The running correlation value using the template from step 602 and the waveform from memory 300 is then calculated at step 604. In other words, the template is "dragged" across the stored waveform as time progresses to perform pattern matching. Correlation identifies the times when the template and the waveform are very similar. Hence, at step 606 those places in the waveform that have a correlation value at a maximum value above a threshold are determined to correspond to the beginning of an oscillation complex. Once the beginning of an oscillation complex is identified at step 606, it is determined at step 608 from, for example, the instantaneous slope of the envelope whether the oscillation data forms an envelope having a suitable pattern for an oscillometric envelope, e.g., there are no abrupt step changes, not too much asymmetry, and the envelope has its characteristic shape. If the envelope is "good", the envelope is analyzed and the blood pressure is calculated at step 610. However, if the envelope is not acceptable, then the threshold is lowered at step 612 and step 606 repeated until a qualified blood pressure envelope is found. If the threshold gets too low, as when the signal is very noisy, the blood pressure calculation stops and the results from step 600 are output.

In accordance with a second embodiment applying correlation in accordance with the invention, the blood pressure waveform is correlated with a predetermined template in real time during the step deflate measurement cycle. In this embodiment, a predetermined template based upon known shapes of cuff blood pressure complexes is used. For example, an oscillation complex taken around MAP during a previous quiet NIBP determination or an oscillation complex recorded previously from a broad patient population and adjusted for heart rate may be used as the template. Any template can be easily adjusted for a change in heart period (rate). This can be done by scaling time so that the old template samples are compressed or expanded to fit the new heart period. When the compression or expansion is done, a linear interpolation for any particular sample may be necessary.

The predetermined template is then correlated with the cuff waveform as the samples are being collected. The correlation value is computed as the data acquisition at each pressure step progresses and is used to determine if enough data has been collected at a given cuff pressure level so that deflation to the next cuff level may occur. In other words, no matching of two waveforms is necessary so long as one waveform sufficiently matches the template. Deflation can thus proceed sooner in many cases.

Preferably, the template is adapted from complex to complex as the NIBP data acquisition process progresses. For example, once a new complex has been identified, it can be used as the new template for further signal processing during the step deflate measurement. This eliminates the afore-mentioned problem caused by ignoring the first complex when there is no amplitude match. Of course, more stringent conditions can be put on the properties of the newly detected oscillation complex before it becomes a template. Also, as in the first embodiment, the threshold and refractory time may be adaptive as well.

Figure 7:
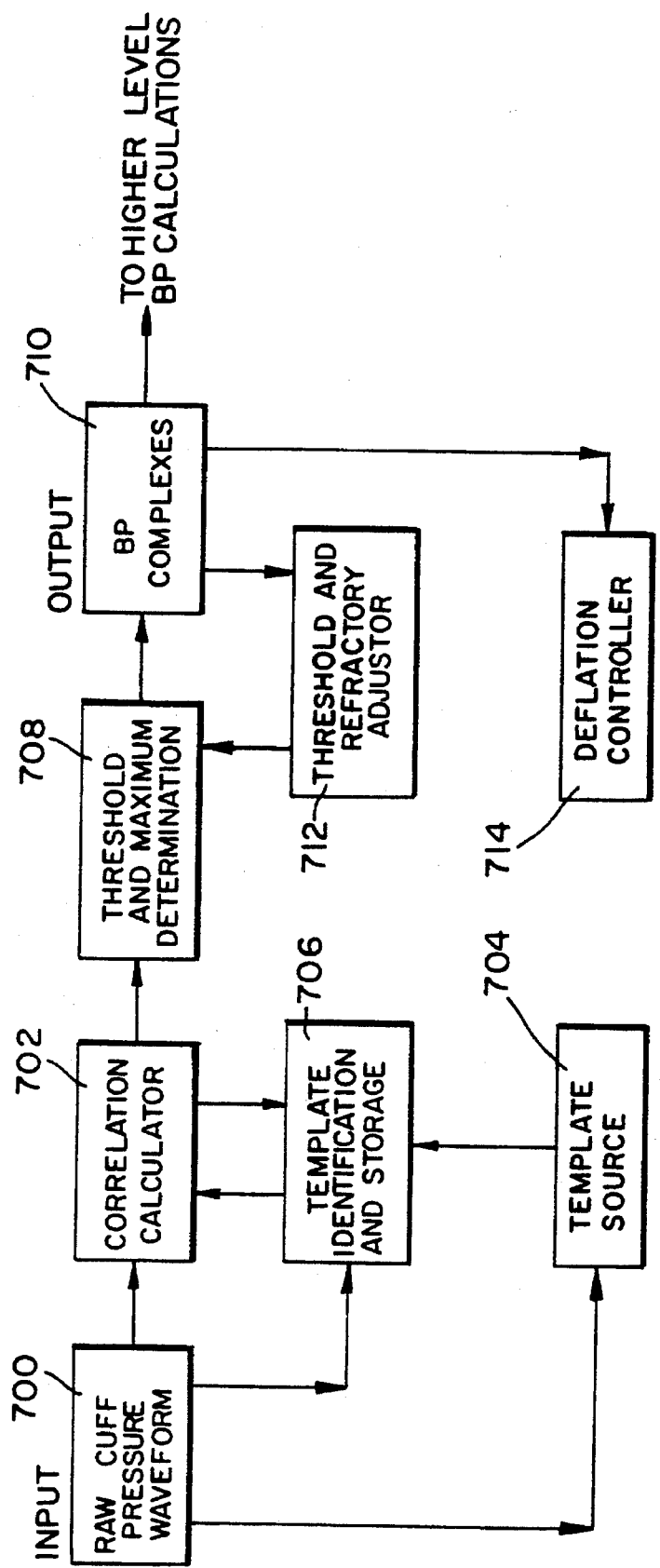
FIG. 7 illustrates the flow of data for real-time analysis of acquired oscillation complexes at each pressure level using correlation techniques in accordance with a second embodiment of the invention.

FIG. 7 illustrates in summary form the data flow for the above-described real-time correlation technique. Generally, the illustrated data flow is provided by software implemented by microprocessor 107, although a dedicated hardware circuit may also be used to implement the illustrated algorithm.

In FIG. 7, the raw cuff pressure waveform 700 received from waveform sample memory 300 or directly from the pressure transducer 104 is provided to a correlation calculator 702. Correlation calculator 702 may, for example, implement the above equations for $C_i$. A template which is either taken from a previous or present NIBP determination or from a predetermined initial template from template source 704 is identified and stored at 706. The stored template is then provided to correlation calculator 702 for the calculation of $C_i$ for all $C_i$. By using samples taken at a quiet time as the template, noisy conditions may be better detected. The maximum of the correlation values $C_i$ for each crossing of the threshold is then determined at 708. Those samples with the maximum correlation value $C_i$ for each crossing of the threshold are determined to correspond to the beginning of an oscillation complex and are output as such at 710. Also, as desired, the threshold may be adjusted at 712 to account for the refractory period or threshold crossings would be ignored to make certain that the detected heart beat periods fall to within a desired range. In addition, once a satisfactory oscillation complex is detected, deflate valve 102 is opened at by deflation controller 714 to deflate the pressure cuff 101 to the next detection level. This process is then repeated for each deflation step.

FIG. 8 illustrates a flow chart for minimizing artifacts in the blood pressure data as it is acquired in accordance with the second embodiment of the invention. As illustrated, a conventional NIBP measurement is performed at step 800 in order to determine the initial template. Then, pressure cuff 101 is inflated about the patient's arm to a pressure above systolic (step 802). Pressure cuff 101 is controlled at step 804 to perform a step deflate, and the above-described correlation analysis is performed on the waveform data at step 806 as the data is received so that an oscillation complex can be quickly identified and the cuff 101 deflated to the next pressure level. This process is repeated until the blood pressure envelope 200 is obtained. Envelope analysis is then performed at step 808 in a conventional manner and the blood pressure calculated from the correlated data is output at step 810.

Figure 9:
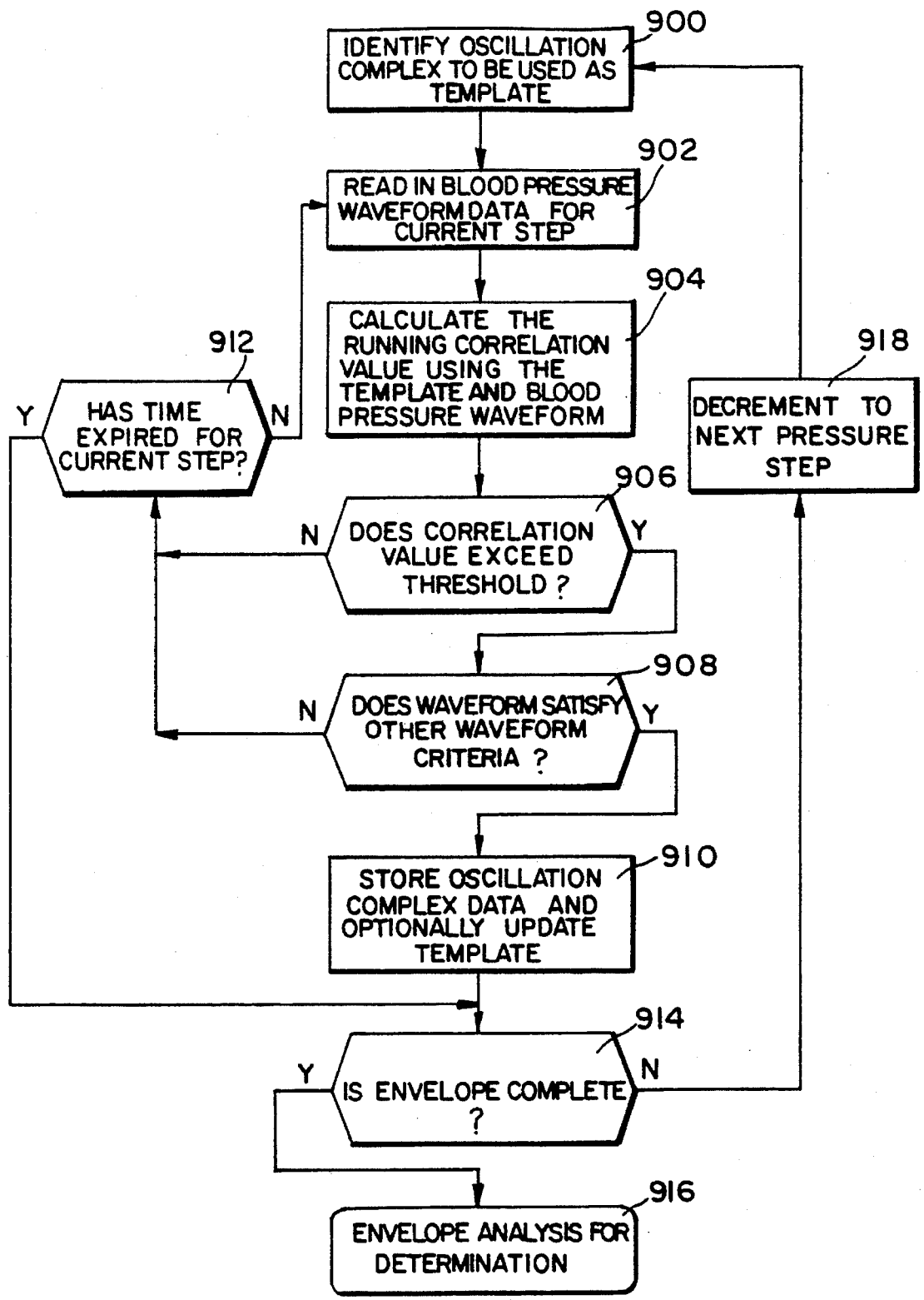
FIG. 9 illustrates a flow chart of a technique for identifying an oscillation complex at each pressure level in noisy conditions using correlation in accordance with the second embodiment of the invention.

FIG. 9 illustrates the correlation technique of the invention for use in a real-time blood pressure determination. Unlike the first embodiment, in this embodiment the correlation continues as long as data acquisition is in progress. As shown in FIG. 9, an oscillation complex to be used as a template is identified at step 900. As just noted, the template may be an oscillation complex from a previous NIBP determination, preferably from the pressure step at which mean arterial pressure occurred. As noted above, by using samples taken at a quiet time as the template, noisy conditions may be better detected. Of course, a more generic template determined from a combination of data from many patients may also be used. Once the template is identified at step 900, the blood pressure waveform data for the current step is read by microprocessor 107 at step 902. The blood pressure waveform data may be read from waveform sample memory 300 or directly from pressure transducer 104. The running correlation value using the template from step 900 and the received waveform samples is then calculated at step 904. In other words, the template is "dragged" across the input waveform as time progresses to perform pattern matching. At step 906, it is determined whether any places in the input waveform have a correlation value above a threshold. If so, it is determined that an oscillation complex may have been found and it is then determined at step 908 using conventional oscillation complex detection techniques whether an oscillation complex has indeed been found. If it is determined at step 908 that an oscillation complex has been found, the oscillation data is stored at step 910. Optionally, if desired, the "found" complex may be used as the template during the next deflation step.

However, if no oscillation complex is found at steps 906 and 908 during a prescribed time for the current deflation step (step 912), microprocessor 107 determines whether it is desired to deflate to the next step. In particular, if it is determined at step 914 that the envelope 200 is complete, conventional envelope analysis and/or envelope analysis including correlation techniques as described above proceeds at step 916. However, if it determined at step 914 that more samples are needed to complete envelope 200, microprocessor opens deflate valve 102 at step 918 to deflate to the next pressure level for detection of another oscillation complex. The template is then updated, as desired, more blood pressure waveform data is then read in at step 902, and the process is repeated.

Figure 11A:
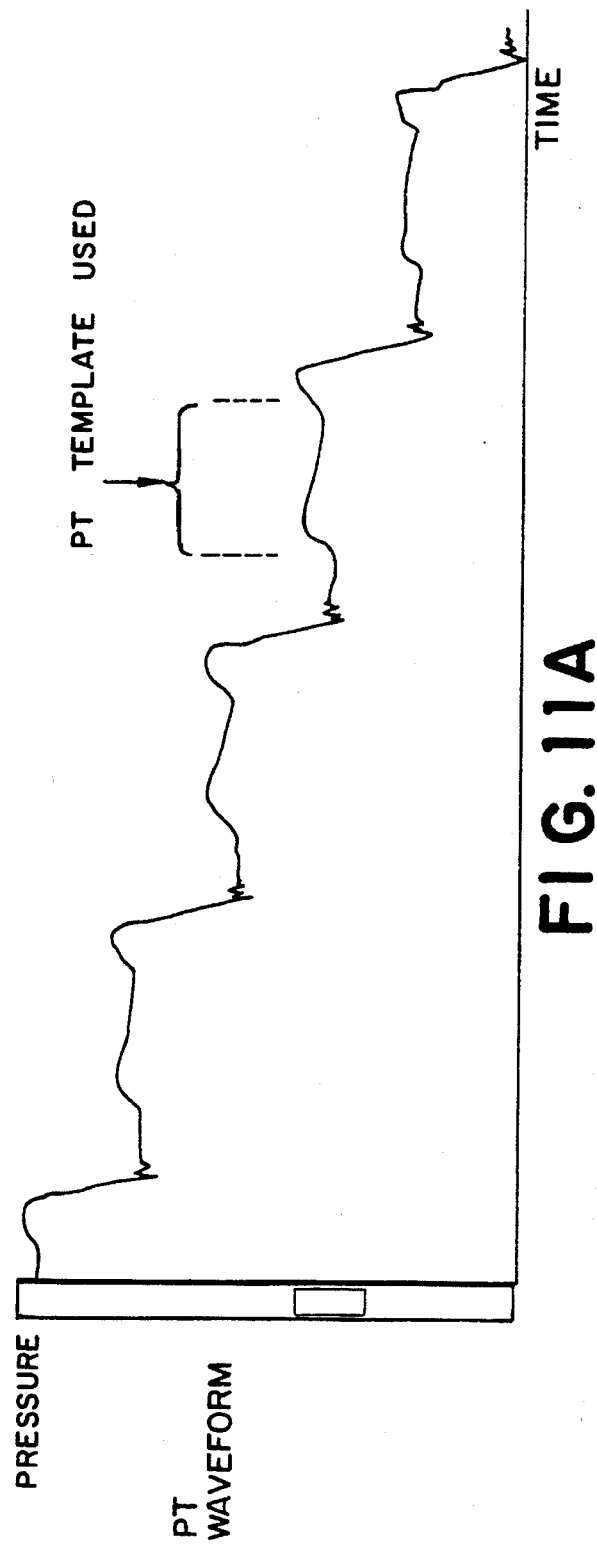
FIGS. 11 (A)–(C) illustrate a correlation determination for a template determined from a composite blood pressure (PT) waveform from the pressure transducer.

FIG. 11(A) illustrates a typical composite (PT) waveform output by pressure transducer 104. The illustrated waveform includes both the DC pressure level for the decremented cuff pressure and the oscillation complexes superimposed thereon. As shown, a portion of the PT signal around MAP is preferably selected as a template for the correlation calculation. FIG. 11(B) illustrates the PT correlation value curve with respect to the same time interval when the illustrated template is "dragged" across the PT curve of FIG. 11(A). Of course, maximum correlation is obtained when the template passes an oscillation complex, irrespective of the amplitude, for the template is primarily dependent upon curve shape, not size. In FIG. 11(B), sharp peaks in the correlation values were not formed; therefore, a second correlation was performed. In the second correlation, the time window in FIG. 11(B) corresponding to the PT template from FIG. 11(A) was "dragged" across the waveform of FIG. 11(B). As expected, the resulting waveform in FIG. 11(C) has much sharper lines.

Although FIGS. 11(A)–(C) illustrate that a template derived from the PT waveform may be used to identify the oscillation complexes, it is presently preferred to use the oscillation (FPT) waveform which has been removed from the composite (PT) waveform. FIG. 12(A) illustrates a sample FPT waveform removed from the PT waveform of FIG. 11(A). As illustrated, the pulse with the largest amplitude (MAP) is selected as a template for correlation purposes.

FIG. 12(B) illustrates the correlation of the template from FIG. 12(A) with the entire waveform of FIG. 12(A). As expected, the maximum correlation occurs for the oscillation complexes; however, in this case, the correlation peaks are sharply defined. By selecting a threshold as indicated, the beginning of each oscillation complex can be readily determined.

In summary, the invention uses correlation to post-process the oscillometric envelope to eliminate artifacts or as another technique to assess the presence of an oscillation complex in a received waveform. For this purpose, a template of a known oscillation complex is selected from a previous NIBP determination, from any step of the present NIBP data acquisition process, or from a standard template for many patients which is adjusted as a function of heart rate. The received waveform (and any noise contained therein) is compared to the template to identify the points at which the oscillation complexes start. Such correlation indicates how well the incoming signal agrees with the template's pattern as time progresses. Correlation thus identifies when the template and the waveform are most similar. If the degree of correlation exceeds a threshold, it is determined that an oscillation complex is present. Of course, the threshold may be adjusted in accordance with signal conditions.

The present invention also represents a highly accurate, though admittedly computation intensive, approach to identifying oscillation complexes. However, modern processor speeds are more than adequate to make the present invention economically viable for most applications.

It will be appreciated by those skilled in the art that the foregoing has set forth the presently preferred embodiments of the invention and illustrative embodiments of the invention but that numerous alternative embodiments are possible without departing from the novel teachings of the invention. For example, those skilled in the art will appreciate that the techniques of the invention may be used for blood pressure monitors in which the pressure is incremented from diastolic as described, for example, in U.S. Pat. No. 4,461,266 to Hood, Jr. et al. In addition, those skilled in the art will appreciate that the techniques of the invention may be used in continuous as well as step inflate/deflate type monitors for determining the oscillometric blood pressure. Accordingly, all such modifications are intended to be included within the scope of the appended claims.

I claim:

1. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any arterial blood pressure oscillations therein;

deflating means operatively coupled to said cuff for selectively relieving pressure from said cuff;

control means for controlling said inflating means to inflate said cuff and said deflating means to deflate said cuff during respective blood pressure determinations of a patient at respective cuff pressure levels;

means for determining an oscillometric envelope comprising arterial blood pressure oscillations detected during said respective blood pressure determinations of said patient at said respective cuff pressure levels;

a waveform memory for storing waveform samples representing said oscillometric envelope; and processing means for correlating said waveform samples stored in said waveform memory with a predetermined template representing attributes of a known arterial blood pressure oscillation of said patient, and for determining the presence of an arterial blood pressure oscillation in said waveform samples based on a result of said correlation.

2. An apparatus as in claim 1, wherein said predetermined template corresponds to an arterial blood pressure oscillation waveform of said patient measured near mean arterial pressure during a previous blood pressure determination of said patient.

3. An apparatus as in claim 1, wherein said predetermined template corresponds to an arterial blood pressure oscillation waveform of said patient measured at one of said respective cuff pressure levels of a current blood pressure determination.

4. An apparatus as in claim 1, wherein said predetermined template corresponds to a previously measured arterial blood pressure oscillation waveform of said patient and said predetermined template is updated to a new template for said patient during a blood pressure determination of said patient.

5. An apparatus as in claim 1, wherein said processing means calculates correlation values $C_i$ indicating a degree of correlation of said waveform samples, $W_i$, from said waveform memory with said predetermined template, $T_i$.

6. An apparatus as in claim 5, wherein said processing means calculates said correlation values $C_i$, $-1 <= C_i <= +1$, in accordance with the equation:

$$C_j = \frac{\sum_i (W_{i+j} - W_j) \cdot (T_i - T)}{\sqrt{\sum_i (W_{i+j} - W_j)^2 \cdot \sum_i (T_i - T)^2}}$$

$$\text{where } W_j = \frac{\sum_i W_{i+j}}{n} \quad T = \frac{\sum_i T_i}{n}$$

and where i and j are time indices, n is a number of samples in said predetermined template, and the summations are from 1 to n.

7. An apparatus as in claim 6, wherein said processing means compares said correlation values $C_i$ with a predetermined threshold L, $-1 <= L <= +1$, and determines that an arterial blood pressure oscillation is present when $C_j > L$.

8. An apparatus as in claim 7, wherein said processing means adjusts said predetermined threshold L during a blood pressure determination.

9. An apparatus as in claim 8, wherein said processing means reduces said predetermined threshold L during said blood pressure determination until a sufficient number of arterial blood pressure oscillations to form an oscillometric envelope are found.

10. An apparatus as in claim 5, wherein said processing means calculates said correlation values $C_i$ in accordance with the equation:

$$C_j = \Sigma W_{i+j} T_i$$

where i and j are time indices and the summation is i from 1 to n.

11. An apparatus as in claim 10, wherein said processing means compares said correlation values $C_i$ with a predetermined threshold L, where L is a function of the energy levels of $W_i$, $T_i$ and noise, and determines that an arterial blood pressure oscillation is present when $C_j > L$.

12. An apparatus as in claim 11, wherein said processing means adjusts said predetermined threshold L during a blood pressure determination.

13. An apparatus as in claim 12, wherein said processing means reduces said predetermined threshold L during said blood pressure determination until a sufficient number of arterial blood pressure oscillations to form an oscillometric envelope are found.

14. A method of determining a patient's blood pressure using an automatic oscillometric blood pressure monitor comprising a cuff, means for inflating and deflating said cuff, means for measuring arterial blood pressure oscillation complexes through measurement of time varying pressures within said cuff, and means for searching for arterial blood pressure oscillation complexes at respective cuff pressure levels, said method comprising the steps of:

selectively inflating and deflating said cuff and detecting arterial blood pressure oscillation complexes at respective cuff pressure levels so as to form an oscillometric envelope comprising arterial blood pressure oscillation complexes of said patient at a plurality of cuff pressure levels;

storing waveform samples representing said oscillometric envelope;

identifying a known arterial blood pressure oscillation complex of said patient as a signal template;

calculating a correlation value for a moving time window of waveform samples indicating a degree of correlation between said signal template and said waveform samples in said moving time window;

identifying time windows for which said signal template and said waveform samples have correlation values above a predetermined threshold; and calculating said patient's blood pressure using said arterial blood pressure complexes from said time windows.

15. A method as in claim 14, wherein said signal template identifying step comprises the step of identifying an arterial blood pressure oscillation waveform of said patient measured near mean arterial pressure during a previous blood pressure determination of said patient.

16. A method as in claim 14, wherein said signal template identifying step comprises the step of identifying an arterial blood pressure oscillation waveform of said patient measured at one of said cuff pressure levels of a current blood pressure determination.

17. A method as in claim 14, wherein said signal template identifying step comprises the step of identifying a previously measured arterial blood pressure oscillation waveform of said patient, and said method comprises the further step of updating said signal template for said patient to a new template during a blood pressure determination of said patient.

18. A method as in claim 14, wherein said calculating step comprises the step of calculating correlation values $C_i$ indicating a degree of correlation of said waveform samples, $W_i$, with said signal template, $T_i$.

19. A method as in claim 18, wherein said calculating step comprises the step of calculating said correlation values $C_i$, $-1 <= C_i <= +1$, in accordance with the equation:

$$C_j = \frac{\sum_i (W_{i+j} - W_j) \cdot (T_i - T)}{\sqrt{\sum_i (W_{i+j} - W_j)^2 \cdot \sum_i (T_i - T)^2}}$$

$$\text{where } W_j = \frac{\sum_i W_{i+j}}{n} \quad T = \frac{\sum_i T_i}{n}$$

and where i and j are time indices, n is a number of samples in said predetermined template, and the summations are from 1 to n.

20. A method in claim 19, wherein said time windows identifying step comprises the steps of comparing said correlation values $C_i$ with a predetermined threshold L, $-1 <= L <= +1$, and determining that an arterial blood pressure oscillation is present when $C_j > L$.

21. A method as in claim 20, comprising the further step of adjusting said predetermined threshold L during a blood pressure determination.

22. A method as in claim 21, comprising the further step of reducing said predetermined threshold L during said blood pressure determination until a sufficient number of arterial blood pressure oscillations to form an oscillometric envelope are found.

23. A method as in claim 18, wherein said calculating step comprises the step of calculating said correlation values $C_i$ in accordance with the equation:

$$C_j = \Sigma W_{i+j} \cdot T_i$$

where i and j are time indices and the summation is i from 1 to n.

24. A method as in claim 23, wherein said time windows identifying step comprises the steps of comparing said correlation values $C_i$ with a predetermined threshold L, where L is a function of the energy levels of $W_i$, $T_i$ and noise, and determining that an arterial blood pressure oscillation is present when $C_i > L$.

25. A method as in claim 24, comprising the further step of adjusting said predetermined threshold L during a blood pressure determination.

26. A method as in claim 25, comprising the further step of reducing said predetermined threshold L during said blood pressure determination until a sufficient number of arterial blood pressure oscillations to form an oscillometric envelope are found.

27. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any arterial blood pressure oscillations therein;

deflating means operatively coupled to said cuff for selectively relieving pressure from said cuff;

control means for controlling said inflating means to inflate said cuff and said deflating means to deflate said cuff during respective blood pressure determinations of a patient at respective cuff pressure levels;

means for determining an oscillometric envelope comprising arterial blood pressure oscillations detected during said respective blood pressure determinations of said patient at said respective cuff pressure levels;

a waveform memory for storing waveform samples representing said oscillometric envelope; and processing means for correlating said waveform samples stored in said waveform memory with a standard arterial blood pressure oscillation waveform which is adjusted to each patient as a function of the patient's heart rate, and for determining the presence of an arterial blood pressure oscillation in said waveform samples based on a result of said correlation.

28. A method of determining a patient's blood pressure using an automatic oscillometric blood pressure monitor comprising a cuff, means for inflating and deflating said cuff, means for measuring arterial blood pressure oscillation complexes through measurement of time varying pressures within said cuff, and means for searching for arterial blood pressure oscillation complexes at respective cuff pressure levels, said method comprising the steps of:

selectively inflating and deflating said cuff and detecting arterial blood pressure oscillation complexes at respective cuff pressure levels so as to form an oscillometric envelope comprising arterial blood pressure oscillation complexes of said patient at a plurality of cuff pressure levels;

storing waveform samples representing said oscillometric envelope;

identifying a standard arterial blood pressure oscillation waveform which is adjusted to each patient as a function of the patient's heart rate as a signal template;

calculating a correlation value for a moving time window of waveform samples indicating a degree of correlation between said signal template and said waveform samples in said moving time window;

identifying time windows for which said signal template and said waveform samples have correlation values above a predetermined threshold; and calculating said patient's blood pressure using said arterial blood pressure complexes from said time windows.

* * * * *

UNITED STATES PATENT AND TRADEMARK OFFICE
CERTIFICATE OF CORRECTION

PATENT NO. : 5,590,662
DATED : January 7, 1997
INVENTOR(S) : Lawrence T. Hersch and John W. Booth It is certified that error appears in the above-indentified patent and that said Letters Patent is hereby corrected as shown below:

Column 7, line 40, after "becomes" insert --a--.

Column 7, line 45, change "W" to --$W_i$--.

Signed and Sealed this

Fifteenth Day of April, 1997

Attest:

BRUCE LEHMAN

*Attesting Officer*    Commissioner of Patents and Trademarks